United States Patent
Wang et al.

(10) Patent No.: US 9,012,631 B2
(45) Date of Patent: Apr. 21, 2015

(54) 1,3-OXAZOLIDINE-2-ONE-LIKE COMPOUND, PREPARATION METHOD AND USES THEREOF

(75) Inventors: Si-Qing Wang, Jiangsu (CN); Yong Deng, Sichuan (CN); Zai-Xin Chen, Jiangsu (CN); Hui Zhang, Sichuan (CN); Zhi-Pei San, Sichuan (CN); Bai-Yang Mao, Jiangsu (CN); Zheng-Jun Xia, Jiangsu (CN); Long Jiang, Jiangsu (CN); Ming-Guang Zhang, Jiangsu (CN); Song Lin, Jiangsu (CN); Ming-Lin Wang, Jiangsu (CN)

(73) Assignees: Yabang Pharmaceutical Co., Ltd (CN); Jiangsu Yabang Shengyuan Pharmaceutical Co., Ltd (CN); Changzhou Yabang Pharmaceutical Co., Ltd (CN)

( * ) Notice: Subject to any disclaimer, the term of this patent is extended or adjusted under 35 U.S.C. 154(b) by 14 days.

(21) Appl. No.: 14/125,944

(22) PCT Filed: Aug. 10, 2011

(86) PCT No.: PCT/CN2011/078211
§ 371 (c)(1),
(2), (4) Date: Mar. 5, 2014

(87) PCT Pub. No.: WO2012/171248
PCT Pub. Date: Dec. 20, 2012

(65) Prior Publication Data
US 2014/0171640 A1    Jun. 19, 2014

(30) Foreign Application Priority Data
Jun. 15, 2011   (CN) .......................... 2011 1 0159445

(51) Int. Cl.
*C07D 263/20*   (2006.01)
(52) U.S. Cl.
CPC .................................. *C07D 263/20* (2013.01)
(58) Field of Classification Search
None
See application file for complete search history.

(56) References Cited

U.S. PATENT DOCUMENTS

2010/0292241 A1   11/2010   Brnardic et al.

FOREIGN PATENT DOCUMENTS

| CN | 1772750 | 5/2006 |
|---|---|---|
| CN | 101774978 | 7/2010 |

OTHER PUBLICATIONS

PCT International Search Report, Mar. 22, 2012, for PCT/CN2011/078211, filed Aug. 10, 2011.
PCT Written Opinion, Mar. 22, 2012, for PCT/CN2011/078211, filed Aug. 10, 2011.
Brickner et al., "Synthesis and antibacterial activity of U-100592 and U-100766, two oxazolidinone antibacterial agents for the potential treatment of multidrug-resistant gram-positive bacterial infections . . . " Journal of Medicinal Chemistry, 1996, 39(3): 673-679.
Chen et al., "Graphical Synthetic Routes of Linezolid.", Chinese Journal of Pharmaceuticals, 2010, 41(1): 62-63.
Chinnam Naidu et al., "DMAP-catalyzed synthesis of 2-oxazolidinones from corresponding halohydrins using KOCN/DMF", Tetrahedron Letter, 2010, 51(8):1226-9.
He and Zhang. "The Synthesis of Oxazolidinone Antibiotics [J].", World Notes on Antibiotics, 2009, 30(2): 82-88.
Perrault et al., "The Synthesis of N-Aryl-5(S)-aminomethyl-2-oxazolidinone Antibacterials and Derivatives in One Step from Aryl Carbamates.", Organic Process Research & Development, 2003, 7(4): 533-546.
Morán-Ramallal et al., "Regioselective and stereospecific synthesis of enantiopure 1,3-oxazolidin-2-ones by intramolecular ring opening of 2-(Boc-aminomethyl)aziridines. Preparation of the antibiotic linezolid.", Organic Letters., 2008, 10(10):1935-8.

*Primary Examiner* — Kamal Saeed
(74) *Attorney, Agent, or Firm* — Law Offices of Albert Wai-Kit Chan, PLLC

(57) ABSTRACT

This invention provides 1,3-oxazolidin-2-one compounds of formula I and their salts, their preparation methods, and use in the preparation of linezolid racemate and its optical isomer, which are used as oxazolidinone antibacterial agents. In the formula, R is H, hydroxyl, halogen, $C_1$-$C_{12}$ alkyl, $C_1$-$C_{12}$ alkoxy, nitro and carboxyl; and R can be placed at any position on the benzene rings; and the compound is a racemate or an optical isomer.

16 Claims, No Drawings

1,3-OXAZOLIDINE-2-ONE-LIKE COMPOUND, PREPARATION METHOD AND USES THEREOF

RELATED APPLICATION

This application is the National Stage of International Application No. PCT/CN2011/078211, filed Aug. 10, 2011, which claims the priority of Chinese Application No. 201110159445.0, filed Jun. 15, 2011. The entire contents and disclosures of the preceding applications are hereby incorporated by reference into this application.

FIELD OF THE INVENTION

This invention belongs to the field of medicinal chemistry and relates to 1,3-oxazolidin-2-one compounds (I), their salts, their preparation methods, and their uses in the preparation of racemic mixture and optical isomers of linezolid, an oxazolidinone-antibiotic drug.

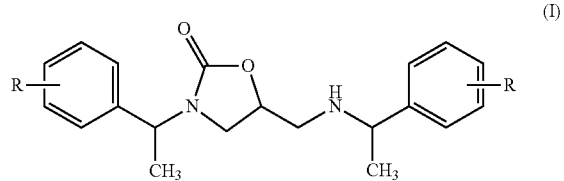

(I)

In the above structural formula, R represents H, hydroxyl, halogen, $C_1$-$C_{12}$ alkyl, $C_1$-$C_{12}$ alkoxy, nitro or carboxyl; R can be placed at any possible position on the benzene rings; and the compound is a racemate or an optical isomer.

BACKGROUND OF THE INVENTION

Linezolid, with a chemical name of (S)—N-{[(5S)-3-[3-fluoro-4-(4-morpholinyl)phenyl]-2-oxo-1,3-oxazolidin-5-yl]methyl}acetamide, is a new oxazolidinone antibiotic drug developed by Pharmacia & Upjohn. It was first marketed in the United States in April of 2000 under the commercial name of Zyvox for treating pneumonia and complicated skin infection caused by methicillin-resistant *Staphylococcus aureus* (MRSA), and bacteremia caused by vancomycin-resistant enterococci (VREF) or penicillin-resistant *Streptococcus pneumoniae* (PRSP).

At present, methods for synthesis of linezolid have been described in the literature [(1) Chen W, Hu J L, Zhang X X. Graphical Synthetic Routes of Linezolid. Chinese Journal of Pharmaceuticals, 2010, 41(1): 62-63; (2) He B, Zhang Y. The Synthesis of Oxazolidinone Antibiotics [J]. World Notes on Antibiotics, 2009, 30(2): 82-88]. The better methods include: (1) Reacting (S)-epichlorohydrin and benzaldehyde in aqueous ammonia, and hydrolyzing the resulting imine by hydrochloric acid to obtain (2S)-1-amino-3-chloro-2-propanol, to which a diacetyl group is introduced by acetylation. The product is then condensed with N-carbobenzoxy-3-fluoro-4-morpholinyl-aniline under the action of anhydrous lithium tert-butoxide to give linezolid. The yield of Linezolid is about 50%. The raw materials used are readily available and fewer steps are involved. However, this method requires using anhydrous lithium tert-butoxide which is expensive and hygroscopic [Perrault W R, Pearlman B A, Godrej D B et al. The synthesis of N-aryl-5(S)-aminomethyl-2-oxazolidinone antibacterials and derivatives in one step from aryl carbamates. Org Process Res Dev, 2003, 7(4): 533-546]; (2) Reacting (S)-glycidyl butyrate and N-carbobenzoxy-3-fluoro-4-morpholinyl-aniline with butyl lithium at 78° C. to give (S)-3-(3-fluoro-4-morpholinephenyl)-5-(hydroxymethyl)-1,3-oxazolidin-2-one, which is reacted with methanesulfonic acid and azide, and then reduced and acetylated to give linezolid. [Brickner S J, Hutchinson D K, Barbachyn M R, et al. Synthesis and antibacterial activity of U-100592 and U-100766, two oxazolidinone antibacterial agents for the potential treatment of multidrug-resistant gram-positive bacterial infections. J Med Chem, 1996, 39(3): 673-679]. This method involves more steps and stringent reaction conditions, and requires explosive sodium azide. (3) Condensation between 3-fluoro-4-morpholinylphenyl isocyanate and (S)-glycidyl butyrate under the action of lithium bromide and tributylphosphine oxide to obtain the nucleus of (S)-oxazolidinone, which is further converted to Linezolid [Huang Q, Li H, Niu P L et al., Method for preparing (R)—N-(3-fluoro-4-morpholinylphenyl)-oxazoline-5-methanol, CN1772750]. This method involves more steps and expensive raw materials but only achieves a relatively low yield; (4) Reacting 3-fluoro-4-(morpholinyl)bromobenzene and 5-[(S)-(1-phenylethyl)aminomethyl]-(1,3-oxazolidin-2-one) under the action of cuprous iodide, followed by the Ullmann coupling reaction, catalytic hydrogenolysis and acetylation to give linezolid. [Ramallal R M, Liz R, Gotor V. Regio selective and stereo specific synthesis of enantiopure 1,3-oxazolidin-2-ones by intramolecular ring opening of 2-(Boc-amino methyl)aziridines. preparation of the antibiotic linezolid. Org Lett, 2008, 10(10): 1935-1938]. The raw materials used in this method are not readily available and the reaction conditions are stringent.

In summary, the disclosed methods of synthesizing linezolid are limited by their ability to mass produce linezolid due to the relatively high cost as a result of raw materials that are expensive or not readily available, stringent reaction conditions; a large number of reaction steps, low overall yield; production of large amounts of liquid, solid and gaseous wastes during the preparation process; and reactions that require cumbersome operation and follow-up. Therefore, new methods that use cheap and readily available raw materials, require mild reaction conditions and simple operation, achieve high chemical yield and optical purity, and environmentally friendly are needed for the synthesis of linezolid.

SUMMARY OF THE INVENTION

In one embodiment, this invention provides a type of 1,3-oxazolidin-2-one compounds (I) and their salts.

In another embodiment, this invention provides a method of preparing 1,3-oxazolidin-2-one compounds (I) and their salts.

In one embodiment, this invention provides a method of reversing the chirality of the chiral carbon atom at position 5 of the "1,3-oxazolidin-2-one" nucleus of a chiral 1,3-oxazolidin-2-one compound (I).

In another embodiment, this invention provides uses of 1,3-oxazolidin-2-one compounds (I) in preparing racemate and optical isomers of linezolid, an oxazolidinone-like antibiotic drug.

In one embodiment, this invention provides 1,3-oxazolidin-2-one compounds (I) having the general chemical structure of:

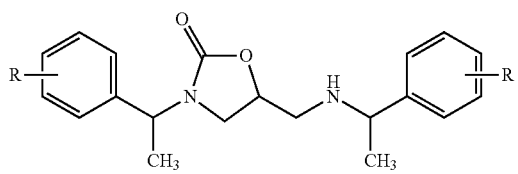

(I)

In the above structural formula, R represents H, hydroxyl, halogen, $C_1$-$C_{12}$ alkyl, $C_1$-$C_{12}$ alkoxy, nitro or carboxyl; R can be placed at any possible position on the benzene rings; and the compound is a racemate or an optical isomer.

The 1,3-oxazolidin-2-one compound (I) described in this invention is a racemate or an optical isomer when the molecule possesses a chiral center; more specifically, the chiral center refers to the carbon atom at position 5 of the "1,3-oxazolidin-2-one" nucleus, the N-linked carbon atom at position 3 of the "1,3-oxazolidin-2-one" nucleus, or the carbon atom that is N-linked to the aminomethyl at position 5 of the "1,3-oxazolidin-2-one" nucleus.

DETAILED DESCRIPTION OF THE INVENTION

The racemate of 1,3-oxazolidin-2-one compounds (I) and its salt described in this invention can be prepared by the method below as illustrated by the following chemical reaction equation wherein R is defined as above:

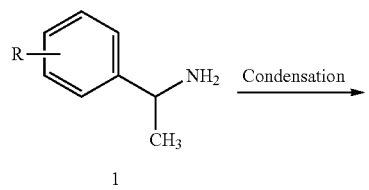

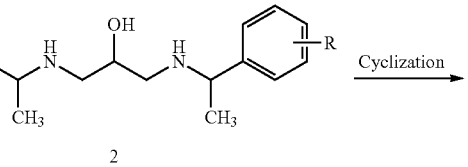

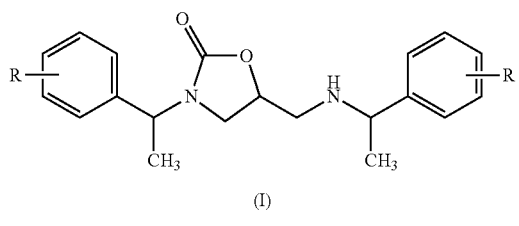

(I)

The racemate of α-phenylethylamine (1) was used as starting material and condensed with epichlorohydrin in the absence or presence of a solvent to obtain the racemate of 1,3-bis-[(1-phenylethyl)amino]-2-propanol (2) which was then cyclized with cyclizing reagents to give racemic 1,3-oxazolidin-2-one (I). Further reaction with an appropriate acid would give a salt of 1,3-oxazolidin-2-one (I).

The optical isomers of 1,3-oxazolidin-2-one compounds (I) and their salts described in this invention can be prepared by the method below as illustrated by the following chemical reaction equation wherein R is defined as above:

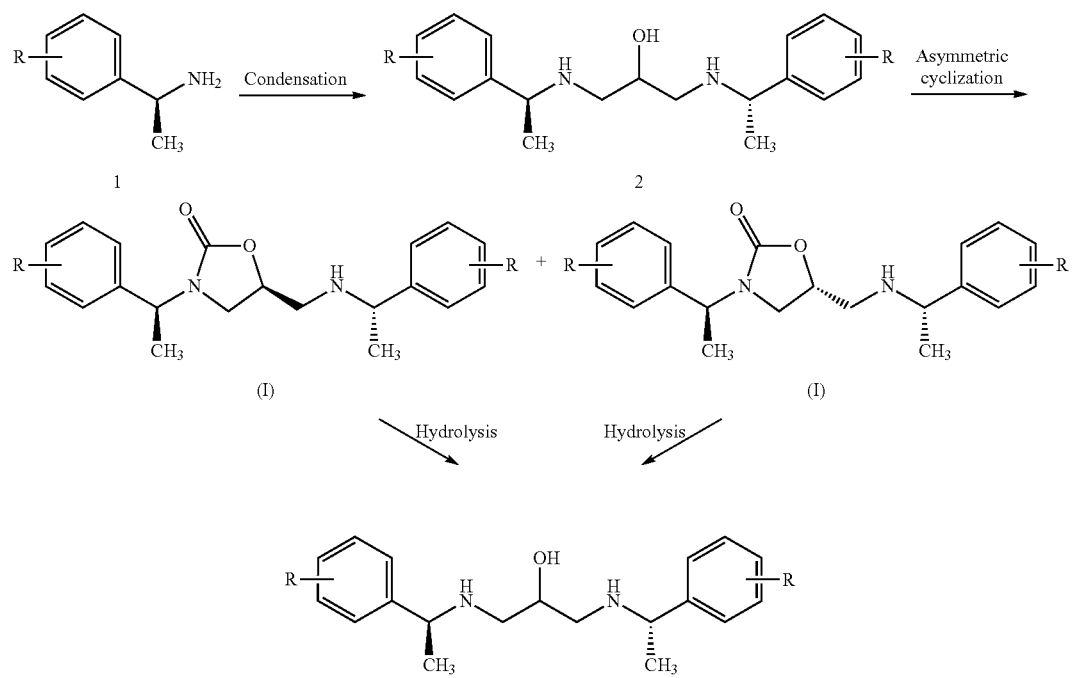

(R) or (S) α-phenylethylamine (1) was used as a starting material and condensed with epichlorohydrin in the absence or presence of a solvent to obtain (R,R) or (S,S) 1,3-bis-[(1-phenylethyl)amino]-2-propanol (2) which, under the action of cyclizing reagents, was asymmetrically cyclized to give a mixture of unequal amounts of (R,R,R) and (R,S,R), or (S,S,S) and (S,R,S) diastereomers from which the optical isomers can be purified using conventional recrystallization or column chromatography. The mixture of diastereomers can also be converted to salts using appropriate acids, and the two isomers can then be separated by conventional recrystallization to obtain the salts of the corresponding optical isomers.

The resulting optical isomer of 1,3-oxazolidin-2-one (I) and its salt, or the mother liquor after recrystallization of one of the isomers, is hydrolyzed under alkaline conditions or neutralized by an alkali after having been hydrolyzed under acidic conditions to give (R,R) or (S,S) 1,3-bis-[(1-phenylethyl)amino]-2-propanol (2), which is then cyclized following the above-mentioned procedures to give 1,3-oxazolidin-2-one (I) having reversed chirality with respect to the chiral carbon atom at position 5 of the "1,3-oxazolidin-2-one" nucleus.

While the methods for synthesizing 1,3-oxazolidin-2-one compound (I), its racemic salts and its optically active salts have been disclosed by the reaction formulae above, the detailed reaction steps will be described below:

(A) Using racemate or optical isomers of α-phenylethylamine (1) as the starting material for condensation with epichlorohydrin in the absence or presence of a solvent and under alkaline condition would give racemate or optical isomers of 1,3-bis-[(1-phenylethyl)amino]-2-propanol (2). The solvent used in the condensation is selected from $C_1$-$C_8$ aliphatic alcohol, $C_3$-$C_8$ aliphatic ketone, N,N-dimethylfomamide, isopropyl ether, 2-Methoxy-2-methylpropane, butylene oxide, dimethoxyethane, ester of $C_1$-$C_6$ fatty acid and $C_1$-$C_6$ aliphatic alcohol, dichloromethane, chloroform, 1,2-dichloroethane, o-dichlorobenzene, benzene, toluene, and acetonitrile. The solvent used is preferably selected from ethanol, isopropanol, isobutanol, 2-butanol, butanone, toluene, and dimethoxyethane. The alkali used in the condensation is selected from hydroxides of alkaline metals or alkaline earth metals, carbonates of alkaline metals or alkaline earth metals, bicarbonates of alkaline metals or alkaline earth metals, piperidine, pyrrolidine, triethylamine, tributylamine, trioctylamine, pyridine, N,N-dimethyl-α-phenylethylamine, N-methyl morpholine, N-methyl piperidine, triethylene diamine, 1,8-diazabicyclo[5.4.0]undec-7-ene, and a combination of these alkalis; said alkali is preferably selected from sodium bicarbonate, potassium carbonate and N-methylmorpholine. Epichlorohydrin is a racemate or an optical isomer. The molar ratio of epichlorohydrin:α-phenylethylamine-like compound (1): alkali is 1.0:1.5-5.0:0.5-3.0, preferably 1.0: 2.0-3.0:1.0-2.0. Temperature for condensation is 50-200° C., and preferably 70-120° C. Time for condensation is 1-48 hours and preferably 5-12 hours.

(B) Racemate or optical isomers of 1,3-bis-[(1-phenylethyl)amino]-2-propanol (2) obtained from step A) is cyclized by an acylating reagent in an appropriate solvent to give a mixture of racemate or optical isomers of 1,3-oxazolidin-2-one (I). The acylating/cyclizing reagent used may be carbonyldiimidazole (CDI), carbonyl chloride, trichloromethyl chloroformate, bis(trichloromethyl)carbonate, ester and the like compound of chloroformic acid and $C_1$-$C_8$ aliphatic alcohol (e.g. ethyl chloroformate, tert-butyl chloroformate and benzyl chloroformate), ester and the like compound from carbonic acid and $C_1$-$C_8$ aliphatic alcohol (e.g. dimethyl carbonate and diethyl carbonate) or disuccinimidyl carbonate (DSC). The solvent used in the acylation/cyclization may be $C_1$-$C_8$ aliphatic alcohol, $C_3$-$C_8$ aliphatic ketone, $C_5$-$C_{10}$ alkane or cyclanes (e.g. n-hexane and n-heptane), N,N-dimethylfomamide, ether (e.g. diethyl ether, diisopropyl ether, methyl tert-butyl ether, tetrahydrofuran, ethylene glycol dimethyl ether), ester of $C_1$-$C_6$ fatty acid and $C_1$-$C_6$ aliphatic alcohol, halogenated hydrocarbon (e.g. dichloromethane, chloroform, 1,2-dichloroethane and o-dichlorobenzene), benzene, toluene, or acetonitrile; Acylation/cyclization can be carried out in one single solvent or a mixture of solvents at a volume ratio of 1:0.1-10. The solvent used is preferably isobutanol, tert-butyl alcohol, butylene oxide, N,N-dimethylfomamide, dimethoxyethane, chloroform, acetone, ethyl ethanoate, or toluene. The molar ratio of acylating/cyclating reagent to 1,3-bis-[(1-phenylethyl)amino]-2-propanol (2) is 0.3-5.0:1.0, preferably 0.4-2.0:1.0. Reaction temperature is −78-150° C., and preferably −20-80° C. Reaction time is 5 minutes to 48 hours, and preferably 15 minutes to 20 hours.

(C) Free base of the two optical isomers of 1,3-oxazolidin-2-one compound (I) can be isolated from the mixture of optically active 1,3-oxazolidin-2-one compounds (I) obtained from step B) by conventional recrystallization or column chromatography. The solvent used in the recrystallization may be $C_1$-$C_6$ aliphatic alcohol, ethers (such as diethyl ether, isopropyl ether, methyl tert-butyl ether and butylene oxide), petroleum ether, $C_3$-$C_8$ aliphatic ketone, $C_5$-$C_{10}$ alkane or cyclanes (e.g. n-hexane and n-heptane), or ester of $C_1$-$C_6$ fatty acid and $C_1$-$C_6$ aliphatic alcohol. Recrystallization can be carried out in one single solvent or a mixture of solvents at a volume ratio of 1:0.1-10. The solvent used is preferably ethanol, ethyl ethanoate, or a mixture of ethyl ethanoate/n-hexane at a ratio of 1:1 (v/v). The eluent used in column chromatography can be a mixture of ethyl ethanoate/ chloroform or ethyl ethanoate/petroleum ether at a ratio of 1-99:99-1 (v/v). The eluent used is preferably a mixture of ethyl ethanoate/chloroform at a ratio of 1:30-70 (v/v) or ethyl ethanoate/petroleum ether at a ratio of 2-6:1 (v/v).

(D) The mixture of optically active 1,3-oxazolidin-2-one (I) obtained from step B) can also be first converted to salts using appropriate acid. The mixture is then purified by conventional recrystallization to obtain salts of optically active 1,3-oxazolidin-2-one (I). The solvent used in recrystallization may be $C_1$-$C_6$ aliphatic alcohol, ethers (e.g. diethylether, isopropylether, methyl tert-butyl ether and butylene oxide), petroleum ether, $C_3$-$C_8$ aliphatic ketone, $C_5$-$C_{10}$ alkane or cyclanes (e.g. n-hexane and n-heptane), or ester of $C_1$-$C_6$ fatty acid and $C_1$-$C_6$ aliphatic alcohol. Recrystallization can be carried out in one single solvent or a mixture of solvents at a volume ratio of 1:0.1-10. The solvent used is preferably ethanol, acetone, ethyl ethanoate, or a mixture of ethyl ethanoate/ n-hexane at 1:1 (v/v).

(E) Free base of 1,3-oxazolidin-2-one (I) obtained from step B) or C) can be converted to salts of 1,3-oxazolidin-2-one (I) using appropriate acids and conventional methods. The acid used may be hydrochloric acid, hydrobromic acid, nitric acid, sulfuric acid, phosphoric acid, formic acid, acetic acid, propionic acid, benzoic acid, oxalic acid, maleic acid, fumaric acid, succinic acid, tartaric acid, citric acid, methanesulfonic acid, ethanesulfonic acid, camphorsulfonic acid, benzenesulfonic acid or p-toluenesulfonic acid.

(F) Free base or salt of optically active 1,3-oxazolidin-2-one (I) obtained from step C), D) or E), or the mother liquor after recrystallization (from which one of the isomers has been isolated) from step D), is hydrolyzed under alkaline conditions, giving (R,R) or (S,S) 1,3-bis-[(1-phenylethyl) amino]-2-propanol (2). The chirality of the carbon atom at position 5 of the "1,3-oxazolidin-2-one" nucleus of 1,3-oxazolidin-2-one (I) is then reversed following the above-mentioned procedures. The alkali used in the hydrolysis may be hydroxides of alkaline metals or alkaline earth metals, carbonates of alkaline metals or alkaline earth metals, bicarbonates of alkaline metals or alkaline earth metals, preferably sodium hydroxide, potassium hydroxide, lithium hydroxide or sodium carbonate. The molar ratio of alkali to 1,3-oxazolidin-2-one compound (I) is 1.0-20.0:1.0, preferably 2.0-10.0:1.0. The solvent used in the hydrolysis may be water, $C_1$-$C_8$ aliphatic alcohol, $C_3$-$C_8$ aliphatic ketone, dioxane, butylene oxide, acetonitrile, or N,N-dimethylfomamide Hydrolysis can be carried out in one single solvent or a mixture of solvents at a volume ratio of 1:0.1-10. Temperature for hydrolysis is 10-150° C., and preferably 50-120° C. Time for hydrolysis is 2-24 hours and preferably 3-10 hours.

The racemate or optical isomers of 1,3-oxazolidin-2-one (I) obtained from above methods can be used for synthesizing the racemate and optical isomers of the oxazolidinoneantibiotic drug—Linezolid, following the route below, wherein R is defined as above:

racemate or optical isomers of 1,3-oxazolidin-2-one (3). Compound (3) can then be purified by conventional recrystallization or column chromatography. To attain a higher purity, compound (3) can also be prepared as inorganic acid salts or organic acid salts which are then manipulated by recrystallization to give a pure batch of inorganic acid salt or organic acid salt. Upon neutralization by an alkali, said pure batch of inorganic acid salt or organic acid salt will give a pure batch of free base. Following the methods described in Ramallal [Ramallal R M, Liz R, Gotor V. Regio selective and stereo specific synthesis of enantiopure 1,3-oxazolidin-2-ones by intramolecular ring opening of 2-(Boc-amino methyl)aziridines. preparation of the antibiotic linezolid. Org Lett, 2008, 10(10): 1935-1938], racemate or optical isomers of compound (3) is then reacted with 3-fluoro-4-(morpholinyl) bromobenzene, through the catalysis of N,N-diaminomethyl ethylenediamine/CuI/$K_2CO_3$ and Ullmann coupling reaction, to give the free base or dihydrochloride of 3-(3-fluoro-4-morpholinylphenyl)-5-[(1-phenylethyl)aminomethyl]-1,

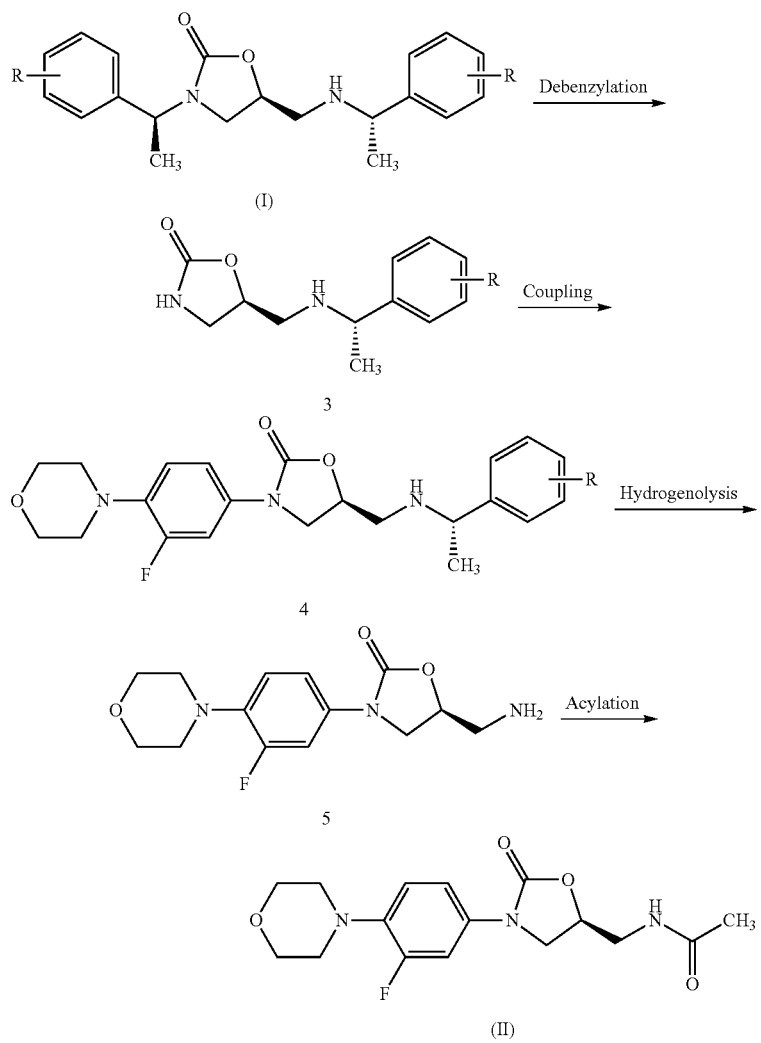

The racemate or optical isomers of 1,3-oxazolidin-2-one (I) obtained from above methods undergoes debenzylation to selectively remove the phenylethyl at position 3 of the "1,3-oxazolidin-2-one nucleus", resulting in the free base of the 3-oxazolidin-2-one (4). Compound (4) is then debenzylated by catalytic hydrogenolysis to give the free base or dihydrochloride of 5-(aminomethyl)-3-[3-fluoro-4-(4-morpholinyl)phenyl]-1,3-oxazolidin-2-one (5). Compound (5) is then acetylated to give the racemate and optical isomers of the oxazolidinone antibiotic drug—Linezolid.

Specific steps for selectively removing the phenylethyl at position 3 of the "1,3-oxazolidin-2-one nucleus" of the racemate or optical isomers of 1,3-oxazolidin-2 (I) are as follows:

The racemate or optical isomers of 1,3-oxazolidin-2-one (I) obtained from the above methods undergoes debenzylation to selectively remove the phenylethyl at position 3 of the "1,3-oxazolidin-2-one nucleus", resulting in the free base of the racemate or optical isomers of 1,3-oxazolidin-2-one (3).

(G) Under acid catalysis in the absence or presence of solvent, the phenylethyl at position 3 of the "1,3-oxazolidin-2-one nucleus" of the racemate or optical isomers of 1,3-oxazolidin-2-one (I) is selectively removed, giving the racemate or optical isomers of 1,3-oxazolidin-2-one (3). The solvent used may be $C_1$-$C_8$ aliphatic alcohol, $C_3$-$C_8$ aliphatic ketone, $C_1$-$C_6$ fatty acid, diethyl ether, diisopropyl ether, methyl tert-butyl ether, butylene oxide, dimethoxyethane, methyl-phenoxide, hexane, heptane, octane, chloroform, or methylene chloride. Solvent used is preferably methyl tert-butyl ether, methyl-phenoxide, or acetic acid. Acid catalyst may be concentrated sulfuric acid, methanesulfonic acid, benzenesulfonic acid, toluenesulfonic acid, or trifluoromethanesulfonic acid. Molar ratio of compound (I) to acid catalyst is 1.0:2.0-30.0, preferably 1.0:6.0-15.0. Reaction temperature is 0-150° C., preferably from room temperature to 80° C.; Reaction time is 1-96 hours, preferably 2-40 hours.

To attain a higher purity of racemate or optical isomers of 1,3-oxazolidin-2-one (3), crude product of the free base of compound (3) can be converted to a salt using an appropriate acid and conventional methods. The salt obtained is then manipulated by recrystallization to give a pure batch of inorganic acid salt or organic acid salt of compound (3). Upon neutralization by an alkali, a pure batch of inorganic acid salt or organic acid salt will give a pure batch of the free base of compound (3).

This invention has the following advantages over the prior art: raw materials used are cheap and readily available, reaction condition is mild, reaction is environmentally friendly, operation is easy, high product yield, low cost, high purity of product, suitable for large-scale preparation of racemate and optical isomers of Linezolid, and etc.

EXAMPLES

This invention will be better understood by reference to the examples which follow. However, the scope of the invention is not limited by the following examples. One skilled in the art will readily appreciate that this invention may be embodied with various modifications without departing from the spirit or essential attributes and scope thereof.

Melting point apparatus: IA6304 (without any calibration of the thermometer); Elements analyzer: Carlo-Erba 1106; Nuclear magnetic resonance spectrometer: Varian INOVA-400 ($CDCl_3$ or DMSO-$d_6$ was used as solvent and TMS as internal standard); High resolution mass spectrometer: Agilent-6210 TOF LC/MS; Automatic polarimeter: Perkin-Elmer model 341. Silica gel plates used in thin-layer chromatography were produced by Shandong Yantai Chemical Industry Research Institute, and UV light or iodine was used for color development; HPLC chiral column: Chiralcel OD-H (250 mm×4.6 mm), with n-hexyl-isopropanol-trifluoroacetic acid as the mobile phase.

Example 1

Preparation of
1,3-bis-[(1-phenylethyl)amino]-2-propanol (2a)

To a reaction flask was successively added 5.87 ml (0.075 mol) of epichlorohydrin, 21.28 ml (0.165 mol) of α-phenylethylamine, 10.363 g (0.075 mol) of potassium carbonate and 120 ml of isopropanol. The mixture was then reacted for 15 hours while being stirred and heated under reflux. After the reaction was completed, the reaction mixture was filtered and the filtered cake was washed with a small amount of ethanol. The filtrate was evaporated under reduced pressure to remove the solvent. The resulting residue was dissolved in 120 ml of dichloromethane and washed successively with 10% aqueous NaOH solution and saturated aqueous NaCl solution. The organic layer was then dried by anhydrous sodium sulfite and filtered, and subsequently put under reduced pressure for solvent removal to give 20.11 g of 1,3-bis[1-phenylethylamino]-2-propanol as a yellowish oil-like substance at a yield of 90%. HR-TOF-MS (+Q) m/z: 299.2120 (calculated $C_{19}H_{26}N_2O+H]^+$: 299.2123).

Example 2

Preparation of
1,3-bis-[(1-phenylethyl)amino]-2-propanol (2a)

The procedure is the same as in Example 1 except that isopropanol was not added and potassium carbonate was replaced by N-methylmorpholine. 1,3-bis-[(1-phenylethyl)amino]-2-propanol was obtained as a yellowish oil-like substance at a yield of 85%. HR-TOF-MS (+Q) m/z: 299.2130 (calculated $[C_{19}H_{26}N_2O+H]^+$: 299.2123).

Example 3

Preparation of the free base and dihydrochloride of
1,3-bis-[(1S)-1-phenylethylamino]-2-propanol (2b)

To a reaction flask was successively added 5.87 ml (0.075 mol) of epichlorohydrin, 25.8 ml (0.2 mol) of α-phenylethylamine, 12.44 g (0.09 mol) of potassium carbonate and 120 ml of toluene. The mixture was then reacted for 18 hours while being stirred and heated under reflux. After the reaction was completed, the reaction mixture was filtered and the filtered cake was washed with a small amount of toluene. The filtrate was evaporated under reduced pressure for solvent removal. The resulting residue was dissolved in 120 ml of dichloromethane and washed successively with 10% aqueous NaOH solution and saturated aqueous NaCl solution. The organic layer was then dried by anhydrous sodium sulfate and filtered, and subsequently put under reduced pressure for solvent removal to give 20.56 g of 1,3-bis-[(1S)-1-phenylethyl)amino]-2-propanol as a yellowish oil-like substance at a yield of 92%. HR-TOF-MS (+Q) m/z: 299.2118 (calculated $[C_{19}H_{26}N_2O+H]^+$: 299.2123).

The free base obtained above was dissolved in 50 ml of ethanol. The pH value of the solution was adjusted to 1-2 by concentrated hydrochloric acid, and the solvent was removed from the solution under reduced pressure. The resulting residue was subjected to recrystallization using ethanol. White needle-shaped crystals of 1,3-bis-[(1S)-1-phenylethylamino]-2-propanol dihydrochloride having a melting point of 267-270° C. were obtained, and at a yield of 86%, $[\alpha]_D^{20}$=−35.5 (c=1.0, MeOH); $^1$H NMR (DMSO-$d_6$, 400 MHz) δ 9.91 (brs, 1H, NH), 9.51 (brs, 2H, 2×HCl), 9.23-9.21 (m, 1H, NH), 7.58-7.37 (m, 10H, ArH), 6.17 (s, 1H, CH(OH)), 4.35-4.28 (m, 3H, CH(OH) and 2×CH(Me)), 2.95-2.68 (m, 4H, 2×$CH_2$), 1.59 (d, 3H, J=3.2 Hz, $CH_3$), 1.58 (d, 3H, J=3.2 Hz, $CH_3$).

Examples 4-10

Preparation of 1,3-bis-[(1-phenylethyl)amino]-2-propanol (2c-2i)

The procedure is the same as in Example 3 except that (S)-α-phenylethylamine was replaced by the corresponding substrates to obtain 1,3-bis-[(1-phenylethyl)amino]-2-propanol (2c-2i) having the following chemical structures (Table 1).

TABLE 1

| Example | α-phenylethylamine | Product | Yield | HR-TOF-MS (m/z, +Q) |
|---|---|---|---|---|
| Example 4 | (4-methylphenyl)-CH(CH₃)-NH₂ | 2c | 90% | 327.2430 [M + H]⁺ |
| Example 5 | (3-methoxyphenyl)-CH(CH₃)-NH₂ | 2d | 88% | 359.2340 [M + H]⁺ |
| Example 6 | (4-methoxyphenyl)-CH(CH₃)-NH₂ | 2e | 85% | 359.2332 [M + H]⁺ |
| Example 7 | (3-nitrophenyl)-CH(CH₃)-NH₂ | 2f | 80% | 389.1829 [M + H]⁺ |
| Example 8 | (4-hydroxyphenyl)-CH(CH₃)-NH₂ | 2g | 75% | 331.2020 [M + H]⁺ |
| Example 9 | (4-chlorophenyl)-CH(CH₃)-NH₂ | 2h | 92% | 367.1338 [M + H]⁺ |
| Example 10 | (4-carboxyphenyl)-CH(CH₃)-NH₂ | 2i | 83% | 387.1915 [M + H]⁺ |

Example 11

Preparation of 3-(1-phenylethyl)-5-[(1-phenylethyl) aminomethyl]-1,3-oxazolidin-2-one (Ia)

To a reaction flask were added 6.10 g (20.49 mmol) of 1,3-bis-[1-phenylethylamino]-2-propanol (2a) and 60 ml of toluene. The mixture was cooled to 0° C. in an ice bath before 6.11 g (37.70 mmol) of carbonyldiimidazole was added and allowed to react for 30 minutes at 0° C. After the reaction was completed, the reaction mixture was washed with 5% aqueous HCl to separate an organic layer. The organic layer was then dried by anhydrous sodium sulfate and filtered, subsequently evaporated under reduced pressure for solvent removal. The residue obtained was subjected to recrystallization using acetone. White needle-shaped crystals of 3-(1-phenylethyl)-5-[(1-phenylethyl)aminomethyl]-1,3-oxazolidin-2-one hydrochloride (racemic hydrochloride of Ia) with a melting point >220° C. were obtained, and at a yield of 89%. The hydrochloride obtained was dissolved in an appropriate amount of dichloromethane and the resulting solution was washed with 10% aqueous NaOH solution to attain an alkaline pH. The resulting organic layer was then dried by anhydrous sodium sulfate and filtered, and subsequently evaporated under reduced pressure for solvent removal to give 3-(1-phenylethyl)-5-[(1-phenylethyl)aminomethyl]-1,3-oxazolidin-2-one (Ia) at a yield of 97%. HR-TOF-MS (+Q) m/z: 325.1912 (Calculated $[C_{20}H_{24}N_2O_2+H]^+$: 325.1916).

Example 12

Preparation of 3-[(1S)-1-phenylethyl]-(5S)-[[(1S)-1-phenylethyl]aminomethyl]-1,3-oxazolidin-2-one ((S,S,S)-Ib) and its hydrochloride To a reaction flask were added 6.10 g (20.49 mmol) of the free base of 1,3-bis-[(1S)-1-phenylethylamino]-2-propanol (2b), 5.9 g (70 mmol) of sodium bicarbonate and 100 ml of dichloromethane. The mixture was cooled to −20° C. in an ice bath before 3.06 g (10.30 mmol) of bis(trichloromethyl)carbonate was added. After 30-minutes of reaction at −20° C., the temperature of the mixture was allowed to return to room temperature. Stirring was continued for 3 hours. After the reaction was completed, the reaction mixture was washed with 5% aqueous HCl to obtain an organic layer. The organic layer was then dried by anhydrous sodium sulfate and filtered, and subsequently evaporated under reduced pressure for solvent removal. The residue obtained was subjected to recrystallization using 40 ml of ethanol. White needle-shaped crystals of 3-[(1S)-1-phenylethyl]-(5S)-[[(1S)-1-phenylethyl] aminomethyl]-1,3-oxazolidin-2-one hydrochloride (hydrochloride of (S,S,S)-Ib) with a melting point >220° C. were obtained, and at a yield of 52% and. $[\alpha]_D^{20}=-99.7°$ (c1.0, CHCl$_3$). The hydrochloride obtained was dissolved in an appropriate amount of dichloromethane and the resulting solution was washed with 10% aqueous NaOH solution to attain an alkaline pH. The resulting organic layer was then dried by anhydrous sodium sulfate and filtered, and subsequently evaporated under reduced pressure for solvent removal to give 3-[(1S)-1-phenylethyl]-(5)-[[(1S)-1-phenylethyl]aminomethyl]-(5S)-1,3-oxazolidin-2-one ((S,S,S)-Ib) with a melting point of 62-63° C. in the form of a white solid, and at a yield of 99%. $[\alpha]_D^{20}=-80.3°$ (c1.0, CHCl$_3$); $^1$H NMR(CDCl$_3$, 400 MHz) δ 7.38-7.29 (m, 5H, ArH), 7.26-7.09 (m, 5H, ArH), 5.23 (q, 1H, J=7.2 Hz, NCH(Me)), 4.59-4.53 (m, 1H, CH), 3.71 (q, 1H, J=6.4 Hz, CH), 3.42 (t, 1H, J=8.8 Hz, CH$_2$), 2.93 (dd, 1H, J$_1$=6.4 Hz, J$_2$=8.0 Hz, CH$_2$), 2.77 (dd, 1H, J$_1$=3.2 Hz, J$_2$=12.8 Hz, CH$_2$), 2.33 (dd, 1H, J$_1$=5.2 Hz, J$_2$=13.2 Hz, CH$_2$), 1.87 (brs, 1H, NH), 1.56 (d, 3H, J=7.2 Hz, CH$_3$), 1.28 (d, 3H, J=6.4 Hz, CH$_3$); $^{13}$C NMR (CDCl$_3$, 100 MHz) δ 157.48, 145.10, 139.55, 128.61, 128.43, 127.77, 127.08, 127.01, 126.64, 72.64, 57.88, 51.20, 49.86, 42.67, 24.63, 16.46; HR-TOF-MS (+Q) m/z: 325.1909 (Calculated $[C_{20}H_{24}N_2O_2+H]^+$: 325.1916).

Example 13

Preparation of 3-[(1S)-1-phenylethyl]-(5R)-[[(1S)-1-phenylethyl]aminomethyl]-1,3-oxazolidin-2-one ((S,R,S)-Ib)

The ethanol mother liquor of Example 12 was evaporated under reduced pressure for solvent removal. The residue obtained was then dissolved in an appropriate amount of dichloromethane and the resulting solution was washed with 10% aqueous NaOH solution to attain an alkaline pH. The resulting organic layer was then dried by anhydrous sodium sulfate, filtered, and subsequently evaporated under reduced pressure for solvent removal. The residue obtained from the filtration was then purified by silica gel column chromatography (eluent: ethyl acetate/petroleum ether=3:1 (v/v)), giving a colorless oil-like substance of 3-[(1S)-1-phenylethyl]-(5R)-[[(1S)-1-phenylethyl]aminomethyl]-1,3-oxazolidin-2-one ((S,R,S)-Ib) at a yield of 26% (with respect to compound 2b). $^1$H NMR (CDCl$_3$, 400 MHz) δ 7.37-7.24 (m, 10H, ArH), 5.17 (dd, 1H, J$_1$=6.8 Hz, J$_2$=14.0 Hz NCH(Me)), 4.53 (s, 1H, CH), 3.81-3.80 (m, 1H, CH), 3.14 (d, 2H, J=7.6 Hz, CH$_2$), 2.71 (dd, 1H, J$_1$=7.2 Hz, J$_2$=12.8 Hz, CH$_2$), 2.61 (dd, 1H, J$_1$=3.6 Hz, J$_2$=12.4 Hz, CH$_2$), 1.54 (brs, 1H, NH), 1.52 (d, 3H, J=7.2 Hz, CH$_3$), 1.38 (d, 3H, J=6.4 Hz, CH$_3$); HR-TOF-MS (+Q) m/z: 325.1913 (Calculated $[C_{20}H_{24}N_2O_2+H]^+$: 325.1916).

Example 14

Preparation of free base of 1,3-bis-[(1S)-1-phenylethylamino]-2-propanol (2b)

To the ethanol mother liquor of Example 12 were added 3.25 g (58 mmol) of potassium hydroxide and 15 ml of deionized water. The mixture was allowed to react for 5 hours while being stirred and heated under reflux. After the reaction cooled down, the reaction mixture was evaporated under reduced pressure for solvent removal. Then 30 ml of deionized water was added to the residue obtained and extraction with 50 ml of dichloromethane was carried out twice. The organic layer obtained was washed with saturated aqueous NaCl solution and then dried by anhydrous sodium sulfate and filtered, and subsequently put under reduced pressure for solvent removal. A yellowish oil-like substance of 1,3-bis-[(1S)-1-phenylethylamino]-2-propanol was obtained at a yield of 90% (Compound (S,S,S)-Ib synthesized in Example 12 was not counted). HR-TOF-MS (+Q) m/z: 299.2126 (Calculated $[C_{19}H_{26}N_2O+H]^+$: 299.2123).

Example 15

Preparation of inorganic acid salts or organic acid salts of compounds (S,S,S)-Ib and (S,R,S)-Ib (S,S,S)-Ib or (S,R,S)-Ib obtained from Example 12 or 13 respectively was dissolved in an appropriate amount of ethanol. The pH of the resulting solution was then made strongly acidic by adding hydrochloric acid, hydrobromic acid, nitric acid, sulfuric acid, or phosphoric acid. The solution was then evaporated under reduced pressure for solvent removal, giving the inorganic acid salt of the compound. The structure of the product was confirmed by elemental analysis (Differences between the measured and theoretical values of the relative amounts of elements in the compound were less than 0.3%).

(S,S,S)-Ib or (S,R,S)-Ib obtained from Example 12 or 13 respectively was dissolved in an appropriate amount of ethanol Equal molar of organic acid was added, the reaction mixture was stirred at room temperature for 30 minutes before the solvent was evaporated under reduced pressure, giving an organic acid salt of the compound. The structure of the product was confirmed by elemental analysis (Differences between the measured and theoretical values of the relative amounts of elements in the compound were less than 0.3%).

Examples 16-22

Preparation of 1,3-oxazolidin-2-one compounds (Ic-Ii)

The procedure is the same as in Example 12 except that 1,3-bis-[(1S)-1-phenylethylamino]-2-propanol (2b) was replaced b the corresponding substrates and dichloromethane was replaced by the corresponding cyclizing reagent. The mixture of diastereomers can be manipulated by silica gel column chromatography or recrystallization to give optical isomers of 1,3-oxazolidin-2-one compounds (Ic-Ii) having the chemical structures shown in Table 2.

TABLE 2

| Example | Substrate | Cyclizing reagent | Product | Yield | HR-TOF-MS (m/z, +Q) |
|---|---|---|---|---|---|
| Example 16 | 2c | trichloromethyl chloroformate | (S,S,S)-Ic | 55% | 353.2235 [M + H]$^+$ |
|  |  |  | (S,R,S)-Ic | 28% | 353.224 [M + H]$^+$ |
| Example 17 | 2d | ethyl chloroformate | (S,S,S)-Id | 48% | 385.2121 [M + H]$^+$ |
|  |  |  | (S,R,S)-Id | 22% | 385.2125 [M + H]$^+$ |
| Example 18 | 2e | dimethyl carbonate | (S,S,S)-Ie | 56% | 385.2132 [M + H]$^+$ |

TABLE 2-continued
| Example | Substrate | Cyclizing reagent | Product | Yield | HR-TOF-MS (m/z, +Q) |
|---|---|---|---|---|---|
| | | | 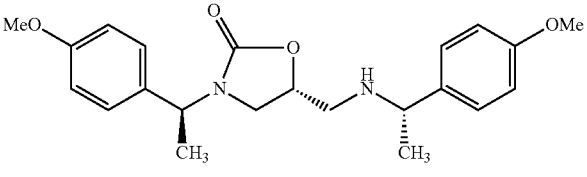<br>(S,R,S)-Ie | 24% | 385.2123 [M + H]⁺ |
| Example 19 | 2f | bis(trichloromethyl) carbonate | <br>(S,S,S)-If | 50% | 415.1622 [M + H]⁺ |
| | | | 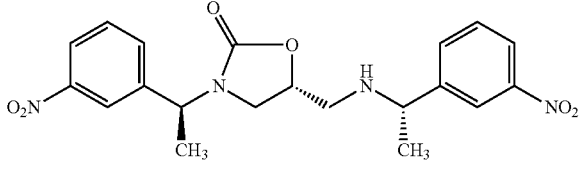<br>(S,R,S)-If | 16% | 415.1615 [M + H]⁺ |
| Example 20 | 2g | CDI | 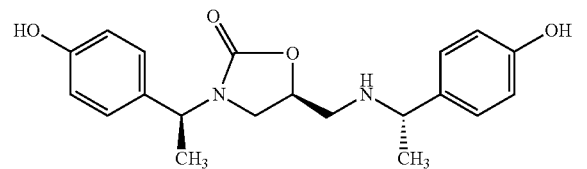<br>(S,S,S)-Ig | 40% | 357.1820 [M + H]⁺ |
| | | | 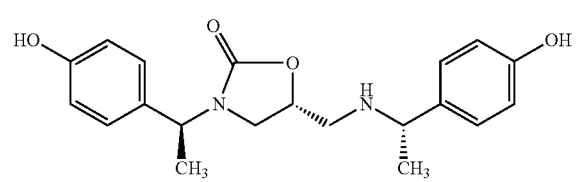<br>(S,R,S)-Ig | 18% | 357.1815 [M + H]⁺ |
| Example 21 | 2h | CDI | 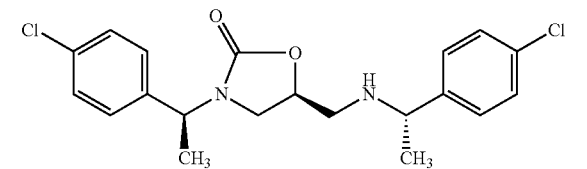<br>(S,S,S)-Ih | 53% | 393.1130 [M + H]⁺ |
| | | | 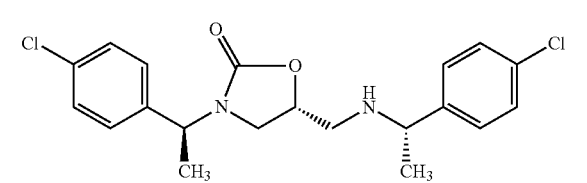<br>(S,R,S)-Ih | 20% | 393.1135 [M + H]⁺ |

TABLE 2-continued

| Example | Substrate | Cyclizing reagent | Product | Yield | HR-TOF-MS (m/z, +Q) |
|---|---|---|---|---|---|
| Example 22 | 2i | CDI | (S,S,S)-Ii | 45% | 413.1716 [M + H]+ |
|  |  |  | (S,R,S)-Ii | 20% | 413.1710 [M + H]+ |

CDI refers to carbonyldiimidazole.

Example 23

Preparation of (5S)—[[(S)-1-phenylethyl]aminomethyl]-1,3-oxazolidin-2-one ((S,S)-3b) and its oxalate To a reaction flask were added 3.75 g (11.54 mmol) of 3-[(1S)-1-phenylethyl]-(5S)-[[(1S)-1-phenylethyl]aminomethyl]-1,3-oxazolidin-2-one ((S,S,S)-Ib), 6.27 ml of anisole, 7.5 ml (115.4 mmol) of methanesulfonic acid. Reaction was carried out at 60° C. for 24 hours with stirring. After the reaction was completed, the reaction mixture was cooled to room temperature and poured into 60 ml of 10% aqueous NaOH solution and extracted with 60 ml of chloroform two times. The organic layer obtained was then washed with saturated aqueous NaCl solution and then dried by anhydrous sodium sulfate and filtered, and subsequently evaporated under reduced pressure for solvent removal. The residue obtained was subjected to recrystallization using 1:1 (v/v) acetone-water to obtain a white solid of (5S)—[[(S)-1-phenylethyl]aminomethyl]-1,3-oxazolidin-2-one ((S,S)-3b) with a melting point of 70-71° C., and at a yield of 95%. $[\alpha]_D^{20}$=–47.2° (c 0.8, CHCl$_3$); $^1$H NMR(CDCl$_3$, 400 MHz) δ 7.36-7.24 (m 5H, ArH), 5.84 (s NH), 4.80-4.74 (m, 1H CH), 3.87-3.83 (q, IH, J=6.4 Hz CH), 3.57 (t. 1H J=8.4 Hz, CH2), 3.42 (t, IH, J=8.0 Hz, CH2), 2.85 (dd, 2H J$_1$=4.0 Hz, J$_2$=13.2 Hz, CH$_2$), 2.65-2.60 (m, IH, NH), 1.40 (d, 3H, J=6.4 Hz, CH$_3$); $^{13}$C NMR (CDCl$_3$, 100 MHz) δ 160.5, 144.8, 128.5, 127.0, 126.4, 75.8, 57.6, 49.7, 43.4, 24.0; HR-TOF-MS (+Q) m/z: 221.1282 (Calculated [C$_{12}$H$_{16}$N$_2$O$_2$+H]$^+$: 221.1290).

11 mmol of the free base of (S,S,S)-Ib was dissolved in an appropriate amount of ethanol before 1.5 g of oxalic acid monohydrate was added. The mixture was allowed to react at room temperature for an hour with stirring. The reaction mixture was then filtrated and the filtered cake was washed with a small amount of ethanol and dried. An oxalate of (5S)—[[(S)-1-phenylethyl]aminomethyl]-1,3-oxazolidin-2-one ((S,S)-3b) with a melting point of 205-206° C. was obtained as a white solid, and at a yield of 96%. $[\alpha]_D^{20}$=–52.5° (c 1.0, H$_2$O);] $^1$H NMR (D$_2$O, 400 MHz) δ 7.54 (s, 5H, ArH), 5.10-5.04 (m, 1H, CH), 4.57-4.52 (q, 1H, J=6.8 Hz, CH), 3.83-3.78 (m, 1H CH$_2$), 3.34-3.15 (m, 1H, CH$_2$), 3.43-3.40 (m, 2H, CH$_2$), 2.06 (s, 1H, NH), 1.74 (d, 3H, J=7.2 Hz, CH$_3$).

Example 24

Preparation of 5-[1-phenylethyl]aminomethyl]-1,3-oxazolidin-2-one (3a) and its hydrochloride The procedure is the same as in Example 23 except that 3-[(1S)-1-phenylethyl]-(5S)-[[(1S)-1-phenylethyl]aminomethyl]-1,3-oxazolidin-2-one ((S,S,S)-Ib) was replaced by 3-(1-phenylethyl)-5-[(1-phenylethyl)aminomethyl]-1,3-oxazolidin-2-one (Ia racemate), and methanesulfonic acid was replaced by concentrated sulfuric acid. 5-[1-phenylethyl] aminomethyl]-1,3-oxazolidin-2-one (3a) was obtained at a yield of 93%. HR-TOF-MS (+Q) m/z: 221.1288 (Calculated [C$_{12}$H$_{16}$N$_2$O$_2$+H]$^+$: 221.1290). Compound 3a obtained was dissolved in an appropriate amount of ethanol and the pH adjusted to strongly acidic by hydrochloric acid before the solvent was evaporated under reduced pressure. A hydrochloride of 3a was obtained as a white solid at a yield of 98%.

Example 25

Preparation of 5R—[[(S)-1-phenylethyl]aminomethyl]-1,3-oxazolidin-2-one ((R,S)-3b)

The procedure is the same as in Example 23 except that 3-[(1S)-1-phenylethyl]-(5S)-[[(1S)-1-phenylethyl]aminomethyl]-1,3-oxazolidin-2-one ((S,S,S)-Ib) was replaced by 3-[(1S)-1-phenylethyl]-(5R)-[[(1S)-phenylethyl)aminomethyl]-1,3-oxazolidin-2-one ((S,R,S)-1b). 5R—[[(S)-1-phenylethyl]aminomethyl]-1,3-oxazolidin-2-one ((R,S)-3b) was obtained at a yield of 93%. HR-TOF-MS (+Q) m/z: 221.1288 (Calculated [C$_{12}$H$_{16}$N$_2$O$_2$+H]$^+$: 221.1290).

Examples 26-32

Preparation of 1,3-oxazolidin-2-one compounds (3c-3i)

The procedure is the same as in Example 23 except that (S,S,S)-Ib was replaced by the corresponding 1,3-oxazolidin-2-one (Ic-Ii). The resulting products were then purified by silica gel column chromatography or recrystallization to give 1,3-oxazolidin-2-one (3c-3i) having the chemical structures shown in Table 3.

TABLE 3
| Example | Product | Yield | HR-TOF-MS (m/z, +Q) |
| --- | --- | --- | --- |
| Example 26 | 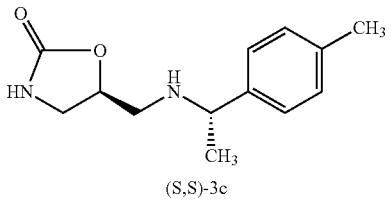<br>(S,S)-3c | 90% | 235.1440 [M + H]⁺ |
|  | 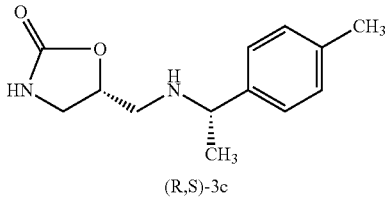<br>(R,S)-3c | 91% | 235.1445 [M + H]⁺ |
| Example 27 | 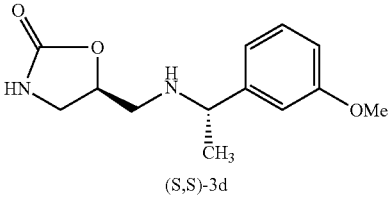<br>(S,S)-3d | 93% | 251.1393 [M + H]⁺ |
|  | 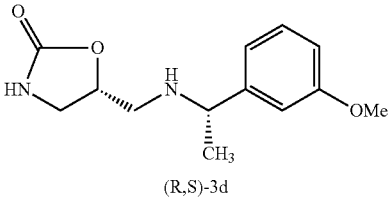<br>(R,S)-3d | 91% | 251.1398 [M + H]⁺ |
| Example 28 | 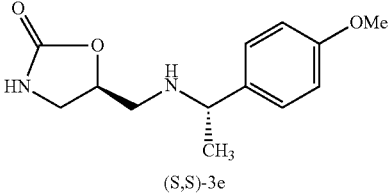<br>(S,S)-3e | 88% | 251.1390 [M + H]⁺ |
|  | 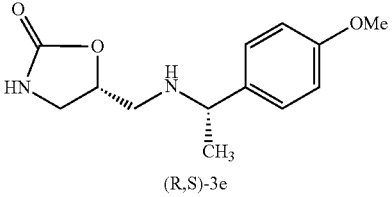<br>(R,S)-3e | 85% | 251.1395 [M + H]⁺ |
| Example 29 | 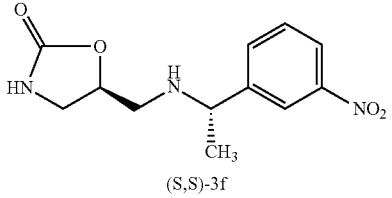<br>(S,S)-3f | 87% | 266.1145 [M + H]⁺ |

TABLE 3-continued

| Example | Product | Yield | HR-TOF-MS (m/z, +Q) |
|---|---|---|---|
| | (R,S)-3f | 88% | 266.1140 [M + H]⁺ |
| Example 30 | (S,S)-3g | 80% | 237.1243 [M + H]⁺ |
| | (R,S)-3g | 78% | 237.1235 [M + H]⁺ |
| Example 31 | (S,S)-3h | 95% | 237.0893 [M + H]⁺ |
| | (R,S)-3h | 94% | 255.0896 [M + H]⁺ |
| Example 32 | (S,S)-3i | 89% | 265.1186 [M + H]⁺ |
| | (R,S)-3i | 88% | 265.1190 [M + H]⁺ |

Example 33

Preparation of 3-(3-fluoro-4-morpholinylphenyl)-5-[(1-phenylethyl)aminomethyl]-1,3-oxazolidin-2-one (4a)

To a reaction flask were added 1.27 g (5.77 mmol) of 3-fluoro-4-morpholiny bromobenzene, 1.5 g (5.77 mmol) of 5-[1-phenylethyl]aminomethyl]-1,3-oxazolidin-2-one (3a), 96 mg (0.51 mmol) of CuI, 1.33 g (9.63 mmol) of anhydrous potassium carbonate, 0.12 ml (1.21 mmol) of N,N-dimethylethylenediamine and 50 ml of toluene. The mixture was allowed to react for 20 hours while being stirred under inert gas. After the reaction was completed, the mixture was cooled to room temperature and 15 ml of deionized water was added to separate the toluene layer which was then washed with saturated aqueous NaCl solution, dried by anhydrous sodium sulfate and filtered. The organic solvent was removed under reduced pressure to give a pale yellowish oil-like substance of 3-(3-fluoro-4-morpholinylphenyl)-5-[(1-phenylethyl)aminomethyl]-1,3-oxazolidin-2-one (4a) at a yield of 85%. HR-TOF-MS (+Q) m/z: 400.2033 (Calculated $[C_{22}H_{26}FN_3O_3+H]^+$: 400.2036).

Example 34

Preparation of the free base and dihydrochloride of 3-(3-fluoro-4-morpholinylphenyl)-5(S)—[[(S)-1-phenylethyl)aminomethyl]-1,3-oxazolidin-2-one ((S,S)-4b)

The procedure is the same as Example 33 except that 5-[1-phenylethyl]aminomethyl]-1,3-oxazolidin-2-one (3a) was replace by (5S)—[[(S)-1-phenylethyl)aminomethyl]-1,3-oxazolidin-2-one ((S,S)-3b). A pale yellowish oil-like substance of the free base of 3-(3-fluoro-4-morpholinylphenyl)-5-[(1-phenylethyl)aminomethyl]-1,3-oxazolidin-2-one ((S,S)-4b) was obtained at a yield of 90%. $[\alpha]^{P}_{20}$=−9.9 (c 1.0, CHCl$_3$): $^1$H NMR (CDCl$_3$, 400 MHz) δ 7.46-6.91 (m, 8H, ArH), 4.68 (m, 1H, CH), 3.88-3.78 (m, 7H, (CH$_2$)$_2$O and CH$_2$ and CH), 3.05 (t, 4H, J=4.4 Hz, (CH$_2$)$_2$N), 2.95 (dd, 1H, J$_1$=3.6 Hz, J$_2$=13.2 Hz, CH$_2$), 2.62 (dd, 1H, J$_1$=5.2 Hz, J$_2$=13.2 Hz, CH$_2$), 1.80 (brs, 1H, NH), 1.36 (d, 3H, J=6.4 Hz, CH3); $^{13}$C NMR (CDCl$_3$, 100 MHz) δ 156.73, 154.45 (d, J=33.4 Hz), 144.94, 136.16 (d, J=8.5 Hz), 133.43 (d, J=10.5 Hz), 128.60, 127.25, 126.07, 118.78 (d, J=3.9 Hz), 113.72 (d, J=3.4 Hz), 107.28 (d, J=26 Hz), 72.15, 66.95, 58.21, 51.03, 49.70, 47.82, 24.55; HR-TOF-MS (+Q) m/z: 400.2039 (Calculated $[C_{22}H_{26}FN_3O_3+H]^+$: 400.2036).

The free base of ((S,S)-4b) obtained above was dissolved in an appropriate amount of ethanol and the pH adjusted to strongly acidic by hydrochloric acid. Resulting mixture was then evaporated under reduced pressure for solvent removal to give a white solid of dihydrochloride of ((S,S)-4b) with a melting point of 247-248° C. and at a yield of 98%. $[\alpha]_D^{20}$=−52.3° (c 0.1, MeOH); $^1$H NMR (DMSO-d$_6$, 400 MHz), δ: 10.50 (brs, 1H, HCl)), 9.48 (m, 1H, NH), 8.62 (brs, 1H, (HCl), 7.61-7.04 (m, 8H, ArH), 5.18-5.11 (m, 1H, CH), 4.42-4.40 (m, 1H, CH), 3.84-3.80 (m, 1H, CH2), 4.13-4.09 (m, 1H, CH2), 3.74-3.71 (m, 4H, (CH$_2$)$_2$O), 3.27-3.21 (m, 1H, Ch2), 3.02-2.95 (m, 6H, CH$_2$ and (CH$_2$)$_2$N), 1.64 (d, 3H, J=6.8 Hz, CH$_3$).

Example 35

Preparation of 3-(3-fluoro-4-morpholinylphenyl)-5(R)—[[(S)-1-phenylethyl)aminomethyl]-1,3-oxazolidin-2-one ((R,S)-4b)

The procedure is the same as in Example 33 except that 5-[1-phenylethyl]aminomethyl]-1,3-oxazolidin-2-one (3a) was replaced by (5R)—[[(S)-1-phenylethyl]aminomethyl]-1,3-oxazolidin-2-one ((R,S)-3b). A pale yellowish oil-like substance of free base of 3-(3-fluoro-4-morpholinylphenyl)-5(R)—[[(S)-1-phenylethyl)aminomethyl]-1,3-oxazolidin-2-one ((R,S)-4b) was obtained at a yield of 87%. HR-TOF-MS (+Q) m/z: 400.2045 (Calculated $[C_{22}H_{26}FN_3O_3+H]^+$: 400.2036).

Examples 36-40

Preparation of 3-(3-fluoro-4-morpholinylphenyl)-5-[(1-phenylethyl)aminomethyl]-1,3-oxazolidin-2-one compound (4c-4h)

The procedure is the same as in Example 33 except that 5-[1-phenylethyl]aminomethyl]-1,3-oxazolidin-2-one (3a) was replaced by the corresponding 1,3-oxazolidin-2-one (3c-3i). Resulting products were then purified by silica gel column chromatography or recrystallization to give 3-(3-fluoro-4-morpholinylphenyl)-5-[(1-phenylethyl)aminomethyl]-1,3-oxazolidin-2-one (4c-4h) having the following chemical structures (Table 4).

TABLE 4

| Example | Product | Yield | HR-TOF-MS (m/z, +Q) |
|---|---|---|---|
| Example 36 | 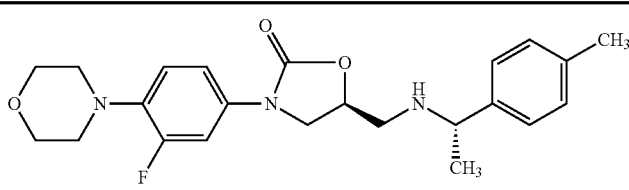 (S,S)-4c | 86% | 414.2197 [M + H]$^+$ |
|  | 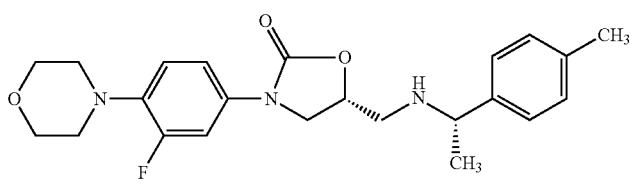 (R,S)-4c | 84% | 414.2190 [M + H]$^+$ |

TABLE 4-continued
| Example | Product | Yield | HR-TOF-MS (m/z, +Q) |
|---|---|---|---|
| Example 37 | 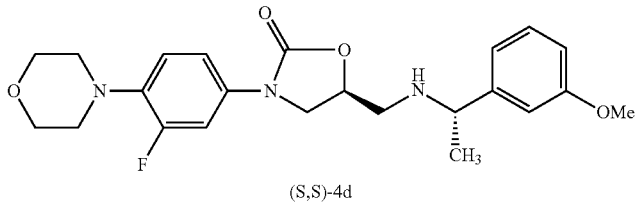 [SMILES: COc1cccc([C@H](C)NC[C@H]2CN(c3ccc(N4CCOCC4)c(F)c3)C(=O)O2)c1 ; "(S,S)-4d"] (S,S)-4d <br> 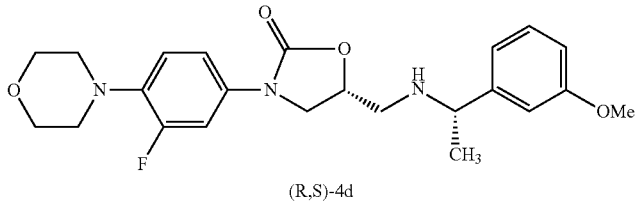 [SMILES: COc1cccc([C@H](C)NC[C@@H]2CN(c3ccc(N4CCOCC4)c(F)c3)C(=O)O2)c1 ; "(R,S)-4d"] (R,S)-4d | 83% <br><br> 85% | 430.2150 [M + H]+ <br><br> 430.2148 [M + H]+ |
| Example 38 | 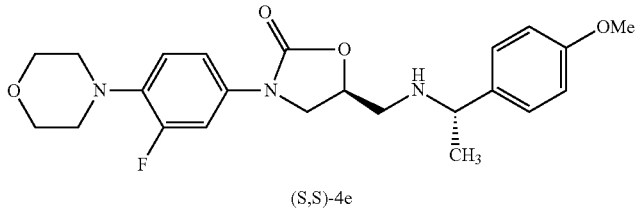 [SMILES: COc1ccc([C@H](C)NC[C@H]2CN(c3ccc(N4CCOCC4)c(F)c3)C(=O)O2)cc1 ; "(S,S)-4e"] (S,S)-4e <br> 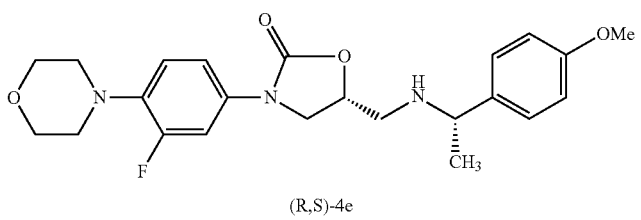 [SMILES: COc1ccc([C@H](C)NC[C@@H]2CN(c3ccc(N4CCOCC4)c(F)c3)C(=O)O2)cc1 ; "(R,S)-4e"] (R,S)-4e | 89% <br><br> 86% | 430.2146 [M + H]+ <br><br> 430.2140 [M + H]+ |
| Example 39 | 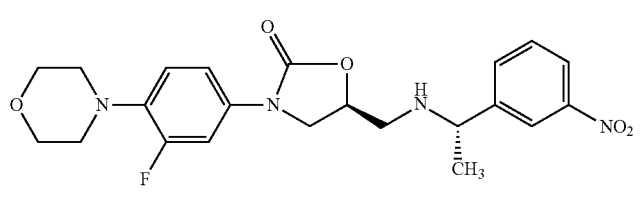 (S,S)-4f <br> 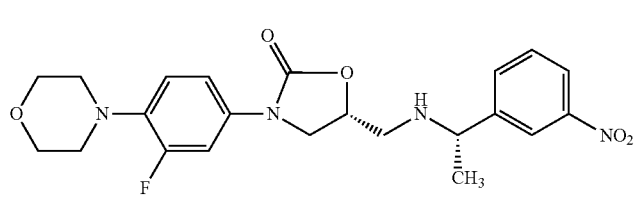 (R,S)-4f | 81% <br><br> 80% | 445.1886 [M + H]+ <br><br> 445.1890 [M + H]+ |
| Example 40 | 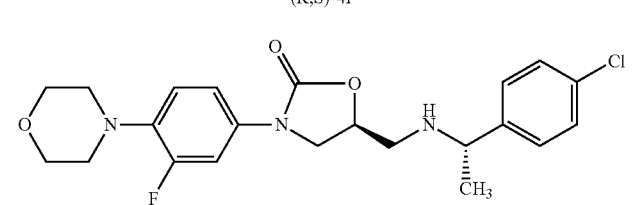 (S,S)-4h | 87% | 434.1643 [M + H]+ |

TABLE 4-continued

| Example | Product | Yield | HR-TOF-MS (m/z, +Q) |
|---|---|---|---|
| | (R,S)-4h | 85% | 434.1652 [M + H]+ |

Example 41

Preparation of dihydrochloride of 3-(3-fluoro-4-morpholinylphenyl-5-aminomethyl-1,3-oxazolidin-2-one (5a)

To a reaction flask were added 3.0 g of dihydrochloride of 3-(3-fluoro-4-morpholinylphenyl)-5-[(1-phenylethyl)aminomethyl]-1,3-oxazolidin-2-one (4a), 100 ml of methanol and 1.0 g of 10% Pd(OH)$_2$/C. Gas inside the reaction flask was evacuated and argon was then introduced to the reaction flask. The reaction mixture was allowed to react for 48 hours at room temperature with stirring. After the reaction was completed, the reaction mixture was filtered, and subsequently put under reduced pressure for solvent removal to give a dihydrochloride of 3-(3-fluoro-4-morpholinylphenyl-5-aminomethyl-1,3-oxazolidin-2-one (5a) as a white solid and at a yield of 95%.

Example 42

Preparation of dihydrochloride of 3-(3-fluoro-4-morpholinylphenyl)-5(S)-aminomethyl-1,3-oxazolidin-2-one ((S)-5b)

The procedure is the same as in Example 41 except that the dihydrochloride of 3-(3-fluoro-4-morpholinylphenyl)-5-[(1-phenylethyl)aminomethyl]-1,3-oxazolidin-2-one (4a) was replaced by 3-(3-fluoro-4-morpholinylphenyl)-5(S)—[[(S)-1-phenylethyl]aminomethyl]-1,3-oxazolidin-2-one ((S,S)-4b). A white solid of dihydrochloride of 3-(3-fluoro-4-morpholinylphenyl)-5(S)-aminomethyl-1,3-oxazolidin-2-one ((S)-5b) with a melting point >220° C. was obtained at a yield of 96%; $[\alpha]_D^{20}$=−53.2° (c 0.1, H$_2$O); $^1$H NMR (D$_2$O, 400 MHz) δ: 7.48 (d, J=14.0 Hz, 1H, ArH), 7.28 (brs, 2H, ArH), 5.16-5.10 (m, 1H, CH), 4.40-4.36 (m, 1H, CH$_2$), 3.97-3.93 (m, 5H, (CH$_2$)$_2$O and CH$_2$), 3.54-3.49 (m, 2H, CH$_2$), 3.17 (brs, 4H, (CH$_2$)$_2$N), NH$_2$ (hidden); TOF-MS (+Q) m/z: 296.15 (Calculated value: 296.14).

Example 43

Preparation of dihydrochloride of 3-(3-fluoro-4-morpholinylphenyl)-5(R)-aminomethyl-1,3-oxazolidin-2-one ((R)-5b)

The procedure is the same as in Example 41 except that the dihydrochloride of 3-(3-fluoro-4-morpholinylphenyl)-5-[(1-phenylethyl)aminomethyl]-1,3-oxazolidin-2-one (4a) was replaced by 3-(3-fluoro-4-morpholinylphenyl)-5(R)—[[(S)-1-phenylethyl)aminomethyl]-1,3-oxazolidin-2-one ((R,S)-4b). A white solid of dihydrochloride of 3-(3-fluoro-4-morpholinylphenyl)-5(R)-aminomethyl-1,3-oxazolidin-2-one ((R)-5b) having a melting point >220° C. was obtained at a yield of 96%; $[\alpha]_D^{20}$=+52.9° (c 0.1, H$_2$O).

Example 44

Preparation of 3-(3-fluoro-4-morpholinylphenyl)-5 (S)-aminomethyl-1,3-oxazolidin-2-one ((S)-5b) and 3-(3-fluoro-4-morpholinylphenyl)-5(R)-aminomethyl-1,3-oxazolidin-2-one ((R)-5b)

The procedure is the same as in Example 41 except that the dihydrochloride of 3-(3-fluoro-4-morpholinylphenyl)-5-[(1-phenylethyl)aminomethyl]-1,3-oxazolidin-2-one (4a) was replaced by the corresponding 3-(3-fluoro-4-morpholinylphenyl)-5-[(1-phenylethyl)aminomethyl]-1,3-oxazolidin-2-one (4c-4h) to give 3-(3-fluoro-4-morpholinylphenyl)-5(S)-aminomethyl-1,3-oxazolidin-2-one ((S)-5b) or 3-(3-fluoro-4-morpholinylphenyl)-5(R)-aminomethyl-1,3-oxazolidin-2-one ((R)-5b).

Example 45

Preparation of the racemate of N-((3-(3-fluoro-4-(4-morpholinyl)phenyl)-2-oxo-5-oxazolidinyl)methyl) acetamide To a reaction flask were added 6.53 mmol of dihydrochloride of 3-(3-fluoro-4-morpholinylphenyl-5-aminomethyl-1,3-oxazolidin-2-one (5a), 100 ml of dichloromethane and 2.95 ml (21.2 mmol) of triethylamine. Then 0.8 ml (8.45 mmol) of acetic anhydride was added while being stirred in an ice-bath. The mixture was then allowed to react at room temperature for 2 hours before being washed successively with 5% aqueous NaOH solution and saturated aqueous NaCl solution. The organic layer was then dried by anhydrous sodium sulfate and filtered, and subsequently put under reduced pressure for solvent removal. The residue was then subjected to recrystallization using ethyl acetate to give white needle crystals at a yield of 85%, HR-TOF-MS (+Q) m/z: 338.1520 (Calculated [C$_{16}$H$_{20}$FN$_3$O$_4$+H]$^+$: 338.1516).

Example 46

Preparation of (S)—N-((3-(3-fluoro-4-(4-morpholinyl)phenyl)-2-oxo-5-oxazolidinyl)methyl)acetamide (Linezolid)

The procedure is the same as in Example 45 except that the dihydrochloride of 3-(3-fluoro-4-morpholinylphenyl-5-aminomethyl-1,3-oxazolidin-2-one (5a) was replaced by dihydrochloride of 3-(3-fluoro-4-morpholinylphenyl)-5(S)-aminomethyl-1,3-oxazolidin-2-one ((S)-5b) to obtain (S)—N-((3-(3-fluoro-4-(4-morpholinyl)phenyl)-2-oxo-5-oxazolidinyl)methyl)acetamide (Linezolid) having a melting point of 78-179° C. and at a yield of 90%; $[\alpha]_D^{20}=-9.1°$ (c 1.0, CHCl3); $^1$H NMR(CDCl$_3$, 400 MHz) δ 7.43 (dd, J$_1$=2.8 Hz, J$_2$=14.4 Hz, 1H, Ar—H), 7.06 (dd, J$_1$=1.6 Hz, J$_2$=8.8 Hz, 1H, Ar—H), 6.94 (t, J=9.2 Hz, 1H, Ar—H), 6.17 (t, J$_1$=6.0 Hz, 1H, NH), 4.80-4.74 (m, IH, CHO), 4.02 (t, J=8.8 Hz, 1H, CH$_2$CHO), 3.86 (t, J=4.8 Hz, 4H, 2×OCH$_2$), 3.75 (dd, J$_1$=6.8 Hz, J$_2$=8.8 Hz, 1H, CH$_2$CHO), 3.71-3.58 (m, 2H, CH$_2$NH), 3.06 (t, J=4.8 Hz, 4H, 2×NCH$_2$), 2.02 (s, 3H, CH$_3$CO); $^{13}$C NMR (CDCl$_3$, 100 MHz) 171.4, 155.7 (d, J=245 Hz), 154.5, 136.4 (d, J=8.8 Hz), 132.8 (d, J=10.4 Hz), 118.6 (d, J=3.9 Hz), 113.8 (d, J=3.0 Hz), 107.4 (d, J=26.1 Hz), 72.0, 66.8, 50.8, 47.5, 41.7, 22.8; HR-TOF-MS (+Q) m/z: 338.1518 (Calculated [C$_{16}$H$_{20}$FN$_3$O$_4$+H]$^+$: 338.1516).

What is claimed is:

1. A compound having the structural formula (I), (3) or (4), or a salt thereof:

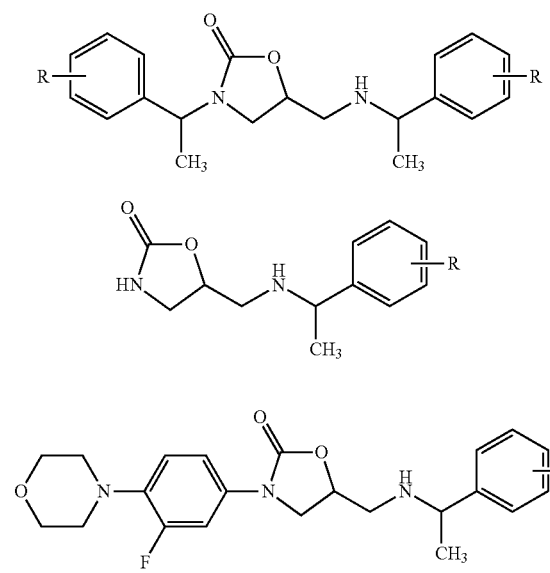

wherein R represents H, hydroxyl, halogen, C$_1$-C$_{12}$ alkyl, C$_1$-C$_{12}$ alkoxy, nitro, or carboxyl; R can be at any position on the benzene rings; and said compound is a racemate or an optical isomer.

2. The compound of claim 1, selected from compounds having the following structural formulae:

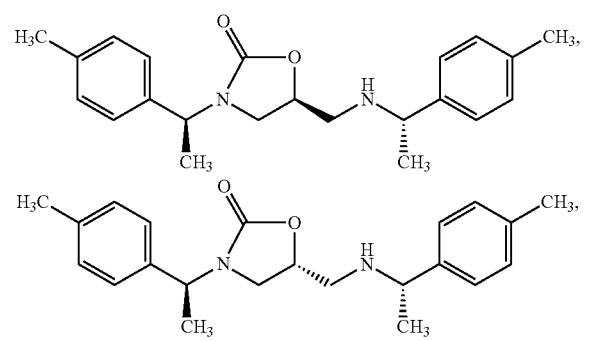

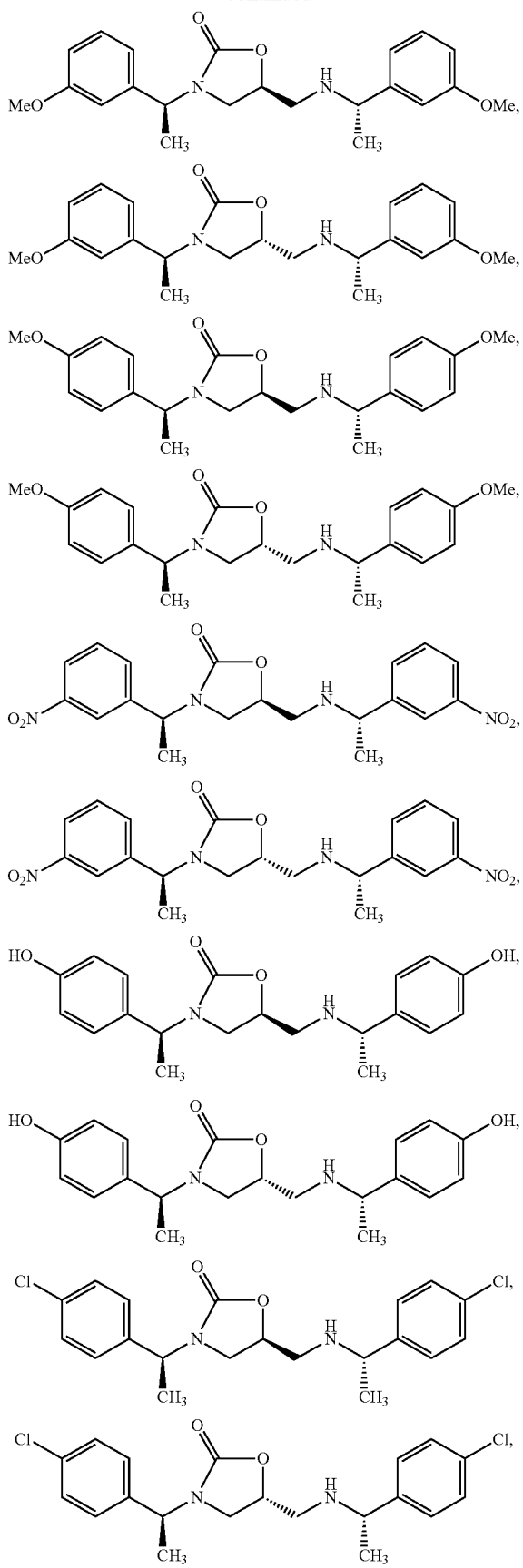

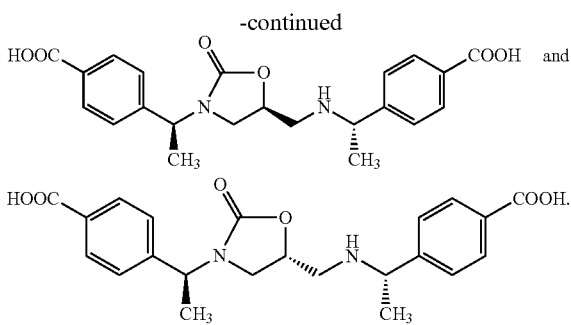

3. A method of preparing a compound having structural formula (I), or its salt,

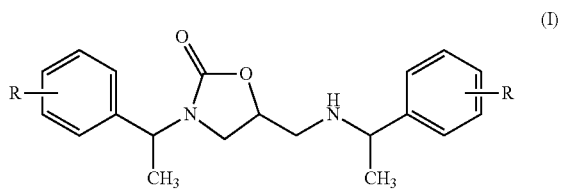

wherein R represents H, hydroxyl, halogen, $C_1$-$C_{12}$ alkyl, $C_1$-$C_{12}$ alkoxy, nitro, or carboxyl; R can be at any position on the benzene rings; and said compound is a racemate or an optical isomer; said method comprising the following steps:
   a) Condensing the racemate or optical isomers of α-phenylethylamine having the structural formula 1 with epichlorohydrin in the absence or presence of a solvent and under alkaline conditions to give the racemate or optical isomers of a compound having the structural formula 2:

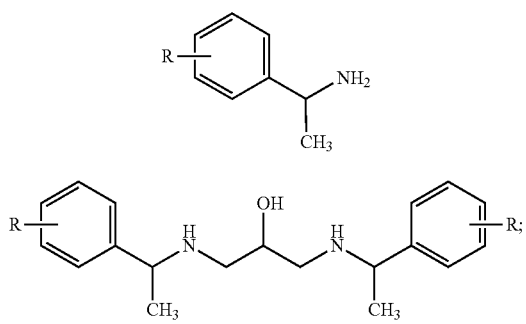

and
   b) Cyclizing the racemate or optical isomers of compound 2 from step a) in the presence of an acylating or cyclizing reagent and solvent to obtain the racemate or optical isomers of compound (I).

4. The method of claim 3, further comprising a step of purifying the optical isomers of compound (I) from step b) by recrystallization or column chromatography to give a free base of the corresponding optically active isomers of compound (I), said free base is optionally reacted with an appropriate acid to give the corresponding salt.

5. The method of claim 3, further comprising the step of preparing a salt of the optical isomers of compound (I) from step b) using an appropriate acid, said salt is optionally purified by recrystallization to give a salt of the corresponding optically active isomer of compound (I).

6. The method of claim 4, further comprising the steps of:
   (i) Hydrolyzing said free base or corresponding salt with alkali to give the (R,R) or (S,S) isomer of compound 2; and
   (ii) Cyclizing said (R,R) or (S,S) isomer from step (i) in the presence of an acylating or cyclizing reagent and solvent to obtain compound (I) with reversed chirality at position 5 of the 1,3-oxazolidin-2-one nucleus compared to compound (I) from step b).

7. The method of claim 3, wherein in step a), said solvent is $C_1$-$C_8$ aliphatic alcohol, $C_3$-$C_8$ aliphatic ketone, N,N-dimethylfomamide, isopropyl ether, 2-Methoxy-2-methylpropane, butylene oxide, dimethoxyethane, ester of $C_1$-$C_6$ fatty acid and $C_1$-$C_6$ aliphatic alcohol, dichloromethane, chloroform, 1,2-dichloroethane, o-dichlorobenzene, benzene, toluene, or acetonitrile; said alkaline conditions are achieved with hydroxides of alkaline metals or alkaline earth metals, carbonates of alkaline metals or alkaline earth metals, bicarbonates of alkaline metals or alkaline earth metals, piperidine, pyrrolidine, triethylamine, tributylamine, trioctylamine, pyridine, N,N-dimethyl-a-phenylethylamine, N-methyl morpholine, N-methyl piperidine, triethylene diamine, 1,8-diazabicyclo[5.4.0]undec-7-ene, or a combination thereof; said epichlorohydrin is a racemate or an optical isomer; the molar ratio of epichlorohydrin:α-phenylethylamine (1):alkali is 1.5-5.0:0.5-3; reaction temperature is 50-200° C.; and reaction time is 1-48 hours.

8. The method of claim 3, wherein in step b), said acylating or cyclizing reagent is carbonyldiimidazole (CDI), carbonyl chloride, trichloromethyl chloroformate, bis(trichloromethyl)carbonate, ester and the like compound of chloroformic acid and $C_1$-$C_8$ aliphatic alcohol, ester and the like compound from carbonic acid and $C_1$-$C_8$ aliphatic alcohol, or disuccinimidyl carbonate (DSC); said solvent is $C_1$-$C_8$ aliphatic alcohol, $C_3$-$C_8$ aliphatic ketone, $C_5$-$C_{10}$ alkane or cyclanes, N,N-dimethylfomamide, diethyl ether, diisopropyl ether, methyl tert-butyl ether, tetrahydrofuran, ethylene glycol dimethyl ether, ester of $C_1$-$C_6$ fatty acid and $C_1$-$C_6$ aliphatic alcohol, dichloromethane, chloroform, 1,2-dichloroethane, o-dichlorobenzene, benzene, toluene, or acetonitrile; reaction is carried out in one solvent or a mixture of solvents at a volume ratio of 1:0.1-10; the molar ratio of said acylating or cyclizing reagent to 1,3-bis-[(1-phenylethyl)amino]-2-propanol (2) is 0.3-5.0:1.0; reaction temperature is −78-150° C.; and reaction time is 5 minutes to 48 hours.

9. The method of claim 4, wherein solvent used in said recrystallization is selected from $C_1$-$C_6$ aliphatic alcohol, diethyl ether, isopropyl ether, methyl tert-butyl ether, butylene oxide, petroleum ether, $C_3$-$C_8$ aliphatic ketone, $C_5$-$C_{10}$ alkane or cyclanes, and ester of $C_1$-$C_6$ fatty acid and $C_1$-$C_6$ aliphatic alcohol; recrystallization is carried out in one solvent or a mixture of solvents at a volume ratio of 1:0.1-10; eluent used in said column chromatography is a mixture of ethyl ethanoate/chloroform, or ethyl ethanoate/petroleum ether at a ratio of 1-99:99-1 (v/v).

10. The method of claim 5, wherein said acid is hydrochloric acid, hydrobromic acid, nitric acid, sulfuric acid, phosphoric acid, formic acid, acetic acid, propionic acid, benzoic acid, oxalic acid, maleic acid, fumaric acid, succinic acid, tartaric acid, citric acid, methanesulfonic acid, ethanesulfonic acid, camphorsulfonic acid, benzenesulfonic acid, or p-toluenesulfonic acid.

11. The method of claim 5, wherein solvent used in said recrystallization is selected from $C_1$-$C_6$ aliphatic alcohol, diethyl ether, isopropylether, methyl tert-butyl ether, butylene oxide, petroleum ether, $C_3$-$C_8$ aliphatic ketone, $C_5$-$C_{10}$ alkane or cyclanes, and ester of $C_1$-$C_6$ fatty acid and $C_1$-$C_6$ aliphatic alcohol; and recrystallization is carried out in one solvent or a mixture of solvents at a volume ratio of 1:0.1-10.

12. The method of claim 6, wherein said alkali in step (i) is selected from hydroxides of alkaline metals or alkaline earth metals, carbonates of alkaline metals or alkaline earth metals, and bicarbonates of alkaline metals or alkaline earth metals; the molar ratio of alkali to compound (I) is 1.0-20.0:1.0; said solvent is selected from water, $C_1$-$C_8$ aliphatic alcohol, $C_3$-$C_8$ aliphatic ketone, dioxane, butylene oxide, acetonitrile and N,N-dimethylfomamide; hydrolysis is carried out in one solvent or a mixture of solvents at a volume ratio of 1:0.1-10; reaction temperature is 10-150° C.; and reaction time is 2-24 hours.

13. A method of preparing the racemate or optical isomers of Linezolid from a compound having structural formula (I), or its salt,

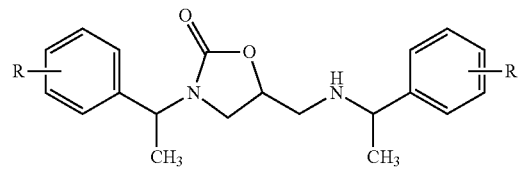

wherein R represents H, hydroxyl, halogen, $C_1$-$C_{12}$ alkyl, $C_1$-$C_{12}$ alkoxy, nitro, or carboxyl; R can be at any position on the benzene rings; and said compound is a racemate or an optical isomer; said method comprising the following steps:

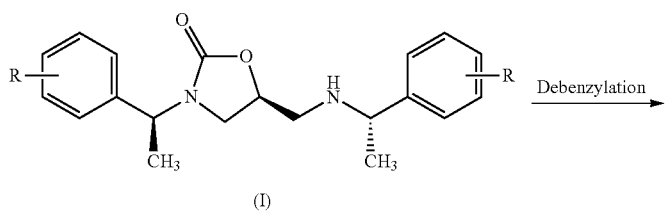

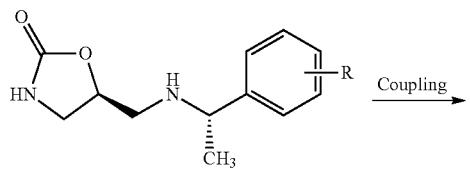

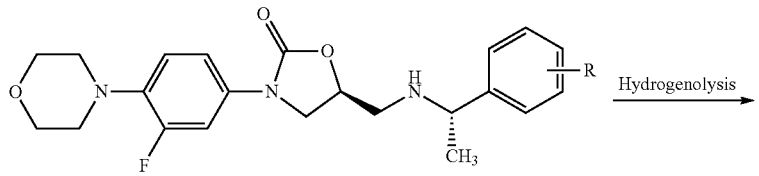

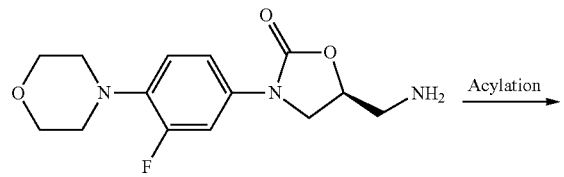

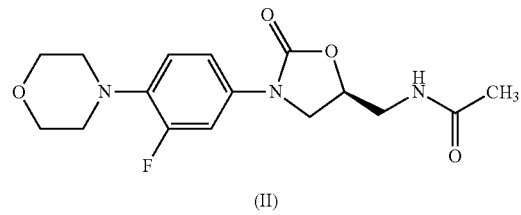

a) selectively removing the phenylethyl group at position of the 1,3-oxazolidin-2-one nucleus of the racemate or optical isomers of compound (I) in the absence or presence of a solvent and under the catalysis of an acid catalyst to obtain the racemate or optical isomers of a compound having the structural formula 3;

b) reacting the racemate or optical isomers of compound 3 from step a) with 3-fluoro-4-(morpholinyl)bromobenzene in the presence of N,N-diaminomethyl ethylenediamine, CuI and $K_2CO_3$, to give a compound having the structural formula 4;

c) removing the benzyl group of compound 4 from step b) under hydrogenolysis to give a compound having the structural formula 5; and d) acetylating compound 5 from step c) in the presence of an acetylating reagent to give the racemate and optical isomers of Linezolid.

14. The method of claim 13, wherein in step a), said solvent is $C_1$-$C_8$ aliphatic alcohol, $C_3$-$C_8$ aliphatic ketone, $C_1$-$C_6$ fatty acid, diethyl ether, diisopropyl ether, methyl tert-butyl ether, butylene oxide, dimethoxyethane, methyl-phenoxide, hexane, heptane, octane, chloroform, or methylene chloride; said acid catalyst is concentrated sulfuric acid, methanesulfonic acid, benzenesulfonic acid, toluenesulfonic acid, or trifluoromethanesulfonic acid; molar ratio of compound (I) to acid is 1.0:2.0-30.0; reaction temperature is 0-150° C.; and reaction time is 1-96 hours.

15. The method of claim 13, further comprising the steps of:
   (i) preparing an inorganic or organic acid salt of compound 3 from step a);
   (ii) purifying said salt from step (i) by recrystallization to obtain a pure batch of salt; and
   (iii) neutralizing said pure batch of salt with alkali to obtain a pure batch of the free base of compound 3.

16. The method of claim 15, wherein said acid salt in step (i) is prepared using hydrochloric acid, hydrobromic acid, nitric acid, sulfuric acid, phosphoric acid, formic acid, acetic acid, propionic acid, benzoic acid, oxalic acid, maleic acid, fumaric acid, succinic acid, tartaric acid, citric acid, methanesulfonic acid, ethanesulfonic acid, camphorsulfonic acid, benzenesulfonic acid, or p-toluenesulfonic acid.

* * * * *